(12) United States Patent  
Ziskin et al.

(10) Patent No.: US 9,239,303 B2
(45) Date of Patent: Jan. 19, 2016

(54) MATERIAL DISCRIMINATION SYSTEM

(75) Inventors: Vitaliy Ziskin, Brighton, MA (US); David Perticone, Winchester, MA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 586 days.

(21) Appl. No.: 13/599,311

(22) Filed: Aug. 30, 2012

(65) Prior Publication Data

US 2013/0056643 A1    Mar. 7, 2013

Related U.S. Application Data

(60) Provisional application No. 61/530,165, filed on Sep. 1, 2011.

(51) Int. Cl.
*G01N 23/083* (2006.01)
*G01V 5/00* (2006.01)
*G01N 23/09* (2006.01)

(52) U.S. Cl.
CPC .............. *G01N 23/09* (2013.01); *G01N 23/083* (2013.01); *G01V 5/0033* (2013.01); *G01N 2223/423* (2013.01)

(58) Field of Classification Search
CPC ... G01N 23/204; G01N 23/09; G01N 23/083; G01N 2223/423; G01V 5/0033
See application file for complete search history.

(56) References Cited

U.S. PATENT DOCUMENTS

| 5,557,108 | A | | 9/1996 | Tumer | |
|---|---|---|---|---|---|
| 5,838,759 | A | * | 11/1998 | Armistead | 378/57 |
| 2006/0093088 | A1 | * | 5/2006 | Sowerby et al. | 378/63 |
| 2009/0067574 | A1 | * | 3/2009 | Johnson | 378/57 |
| 2009/0140150 | A1 | * | 6/2009 | Ivan et al. | 250/361 R |
| 2010/0243874 | A1 | | 9/2010 | Kang | |

FOREIGN PATENT DOCUMENTS

| EP | 1739460 A2 | 1/2007 |
|---|---|---|
| EP | 1882929 B1 | 10/2011 |
| WO | WO9321546 A1 | 10/1993 |

OTHER PUBLICATIONS

Extended European Search Report for European Application No. 12182665.5, mailed Dec. 8, 2014.

* cited by examiner

*Primary Examiner* — Casey Bryant
(74) *Attorney, Agent, or Firm* — Fish & Richardson P.C.

(57) ABSTRACT

This disclosure relates to systems and methods for material discrimination. The systems and methods include a single source that generates both neutrons and photons, and a single imaging array with a common detector that detects the neutrons and the photons generated from the single source. The systems and methods allow for a determination of the contents, and/or the effective atomic number ("Z") of the contents, of an object without physical inspection of the interior of the object.

19 Claims, 8 Drawing Sheets

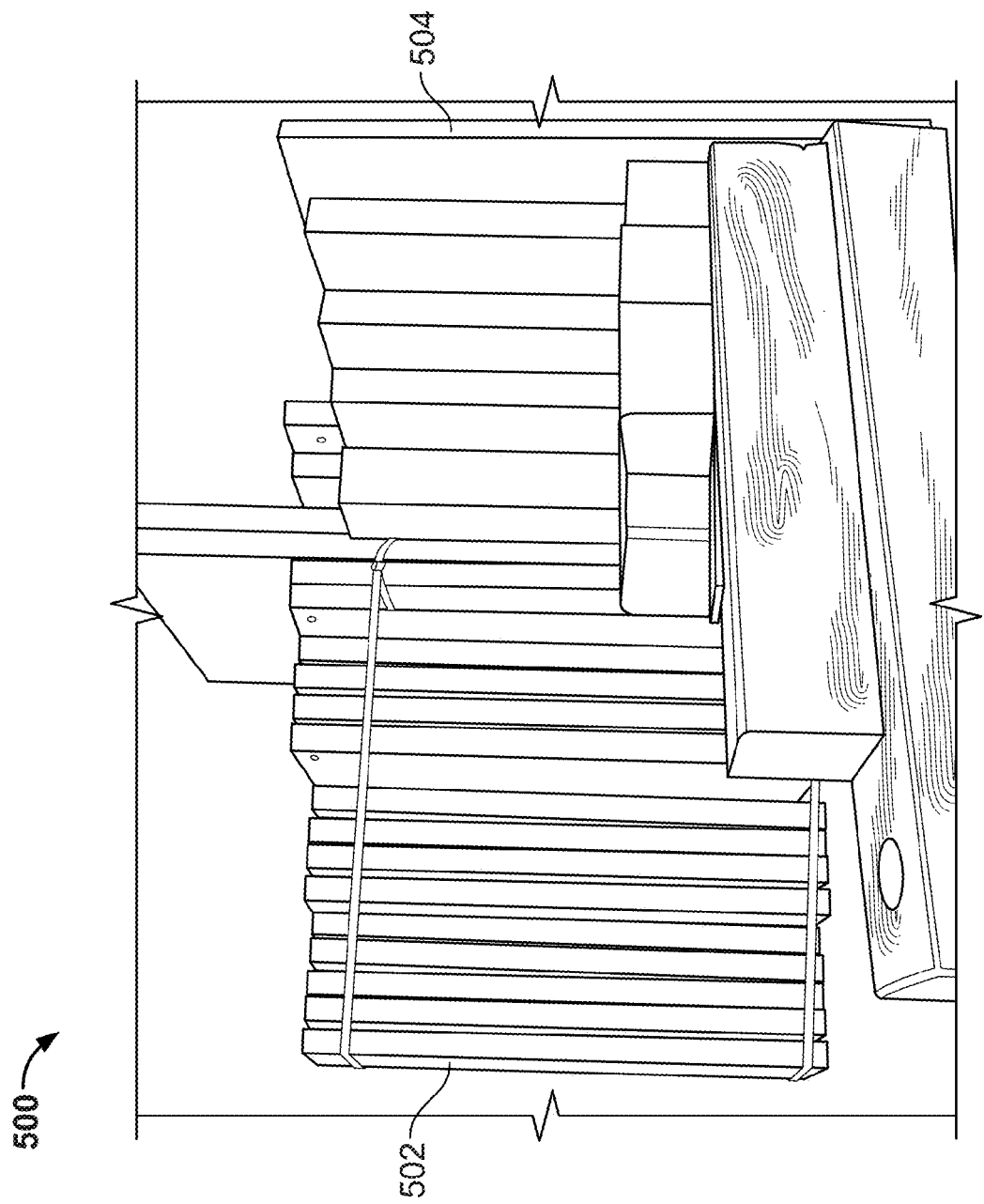

MATERIAL DISCRIMINATION SYSTEM

CROSS-REFERENCE TO RELATED APPLICATIONS

This application claims priority to U.S. Provisional Application Ser. No. 61/530,165, which was filed on Sep. 1, 2011, the entire contents of which are incorporated herein by reference.

TECHNICAL FIELD

This specification generally relates to a material discrimination system, such as may be used in security applications for detecting the presence of concealed hazardous and/or illegal materials.

BACKGROUND

Smuggling of various kinds of contraband has become a widespread problem in the context of global trade and international travel. This issue is particularly difficult to manage in case of import/export of large maritime cargo containers, where it is feasible to physically inspect only a small fraction of the bulk quantity of targets.

In pursuit of a solution to this problem, various passive and active detection techniques have been developed. The passive detection techniques involve identifying natural radioactive emissions emanating from objects of interest. Such passive techniques can be used to detect various types of nuclear materials, but may not be useful in detecting other types of contraband (e.g., illicit materials like drugs, etc.) In contrast to passive detection, the active detection techniques involve interrogating the objects with high energy neutrons and/or photons to ascertain the material distribution and composition of the objects.

SUMMARY

This specification describes technologies related to systems, apparatus, and methods for material discrimination.

In one aspect, the systems, apparatus, and methods disclosed herein feature a materials discrimination system. The materials discrimination system includes a single source configured to produce a beam comprising a neutron constituent and a photon constituent, wherein the neutron constituent and the photon constituent are collinear; a single detector aligned with the single source along a path of the beam, the single detector configured to detect neutrons and photons present in the beam, and to produce a signal based on a detection of neutrons or photons, the signal being associated with a value; and a processor configured to receive the signal produced by the single detector.

In some implementations, the processor is further configured to determine whether the signal represents a detection of a neutron or a photon. Further, in some implementations, determining whether the signal represents a detection of a neutron or a photon comprises comparing the value associated with the signal to a first threshold value and a second threshold value, the second threshold value being greater than the first threshold value. In such implementations, the processor may be configured to determine that the signal represents a photon or a neutron when the value associated with the signal is greater than the first threshold value and less than the second threshold value.

In some implementations, the single source may be a beryllium target that produces the neutron and the photon when struck by a deuteron and the photons may comprise gamma-ray photons or x-ray photons. In some implementations, the single source includes a radio-frequency quadrupole (RFQ) accelerator configured to produce deuterons that create the neutron constituent and the photon constituent. In some versions the neutron constituent and the photon constituent comprise a broad energy distribution.

Some versions involve the neutron constituent having a flux ranging between approximately $10^9$ neutrons/cm$^2$ sec and $10^{11}$ neutrons/cm$^2$ sec. Further, the photon constituent may have a flux ranging between approximately between $10^5$ photons/cm$^2$ sec and $10^8$ photons/cm$^2$ sec in some versions. In some versions, the single source is further configured to produce multi-energy neutrons, and the single source further comprises a second target.

Some versions may involve the single source and the single detector being mounted on a structure comprising an opening configured to receive a cargo. Such versions may include a conveyor configured to move the cargo through the structure and relative to the single source and the single detector. In some versions, the system is re-locatable.

Another aspect involves a system for material discrimination that includes a single source configured to produce a beam comprising a neutron constituent and a photon constituent, wherein the neutron constituent and the photon constituent are collinear; a single imaging array aligned with the single source along a path of the beam, the single imaging array configured to detect neutrons and the photons produced by the single source, and to produce a signal primarily, substantially, or partially based on a detection of neutrons or photons, the signal being associated with a value; and a processor. The processor is configured to receive signals produced by the single detector, distinguish between signals that represent detection of a neutron and signals that represent detection of a photon; generate a first image of a region primarily based on detection of neutrons, and generate a second image of the region primarily based on detection of photons. A display may also be included that is configured to present one or more of the first image or the second image.

In some implementations, the processor is further configured to determine a ratio between the first image and the second image.

Yet another aspect involves a method of material discrimination. The method includes the actions of generating, from a single source, a beam comprising a neutron constituent and a photon constituent, wherein the neutron constituent and the photon constituent are collinear; directing the beam towards a first side of an object to be imaged; detecting, at a single imaging array on a second side of the object, photons and neutrons; identifying a first signal based on detection of photons and a second signal based on detection of neutrons; and generating a first image based on the first signal and a second image based on the second signal. In some versions, the first side of the object and the second side of the object are opposite sides of the object.

Some implementations further involve outputting a graphical representation of one or more of the first image or the second image.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 5 is a second example arrangement of objects to be scanned by a material discrimination system.

Many of the levels, sections and features are exaggerated to better show the features, process steps, and results. Like reference numbers and designations in the various drawings indicate like elements.

DETAILED DESCRIPTION

Figure 1:
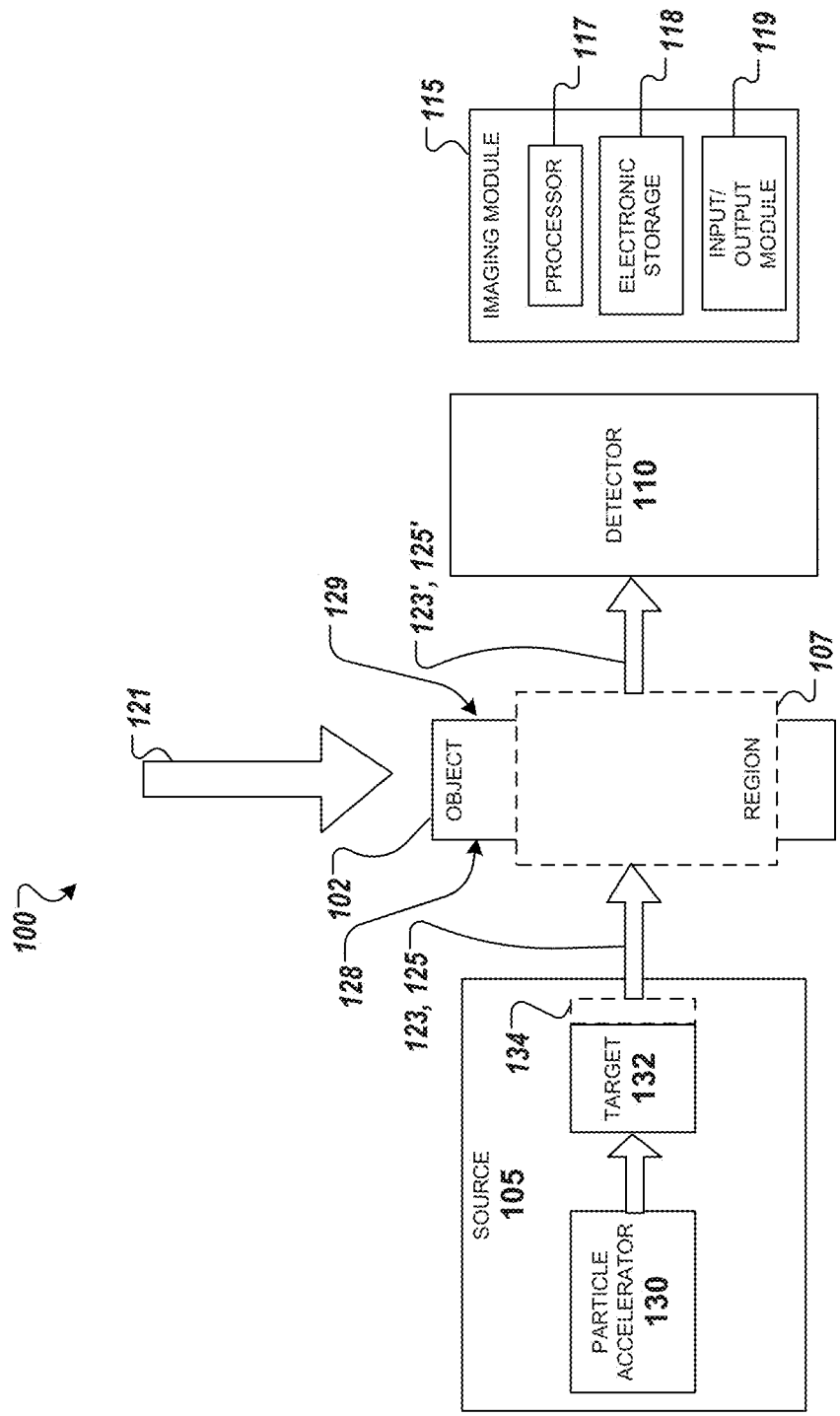
FIG. 1 is a diagram of an example material discrimination system.

This disclosure relates to a material discrimination system including a single source that generates both neutrons and photons, and a single imaging array with a common detector that detects the neutrons and the photons generated from the single source. The system allows for a determination of the contents, and/or the effective atomic number ("Z") of the contents, of an object without physical inspection of the interior of the object. The neutrons and photons can be directed towards an object, such as a cargo container, a suitcase, a vehicle carrying packages, a rail car, a shipping container, an airplane that includes a cargo hold, or any other item that may store items or hold items to be transported. The system may be placed at a location through which such items pass and/or are stored such as, for example, a border crossing, a checkpoint, a rail station or loading depot, a seaport or harbor, or an airport (either to scan planes or luggage). The system may be re-locatable and moveable from one location to another. For example, the system may be re-located from a rail station to an airport.

Neutrons and photons are attenuated differently by a particular material. For example, a material that has a relatively high effective atomic number (a high-Z material) attenuates photons more strongly than neutrons. A high-Z material may have an effective atomic number of approximately twenty or greater. A material that has a relatively low effective atomic number (a low-Z material) attenuates neutrons more strongly than photons. A low-Z material may have an effective atomic number between five and fourteen, for example. By comparing an object's attenuation of photons and its attenuation of neutrons, the approximate effective atomic number of the object may be determined. As a result, imaging, scanning, or otherwise directing neutrons and photons toward an object may allow determination of the object's effective atomic number and, perhaps, identification of the material(s) included in the object without having to unpack the object or otherwise physically inspect the object.

The system of this disclosure generates photons and neutrons from a single source, directs the photons and neutrons towards an object, detects the attenuated photons and neutrons that pass through the object with a single imaging array, discriminates between signals arising from the detection of photons and neutrons respectively, and generates an image of the object's attenuation of photons and an image of the object's attenuation of neutrons. The image of the object's attenuation of photons may be referred to as a "photon-enhanced image" or a "photon image", and the image of the object's attenuation of neutrons may be referred to as a "neutron-enhanced image" or a "neutron image." It should be noted that the enhanced images substantially represent the corresponding particle type (e.g., photon or neutron) but may contain some contamination from other particle types.

The photon-enhanced and neutron-enhanced images may be used to perform material discrimination and/or to determine whether the attenuation is due to organic or metallic materials. High-Z materials may be materials that are nuclear materials or used to shield nuclear materials. Low-Z materials may include illicit drugs and smuggled foodstuffs. Thus, the images may be used to identify whether the object contains hazardous and/or illegal items such as illicit drugs, metallic weapons, weaponizable materials, or nuclear materials, or materials that may be associated with hazardous and/or illegal items, such as metallic shielding used to conceal a radioactive item. By highlighting organic and metallic objects in an image, cargo anomalies can be detected, visually or algorithmically.

FIG. 1 shows a diagram of an example material discrimination system 100. The system 100 images an object 102 by scanning the object with photons and neutrons produced by a source 105 when the object 102 is within or partially in a region 107.

The system 100 includes the source 105, a detector 110, and an imaging module 115. The imaging module 115 includes a processor 117, an electronic storage 118, and an input/output module 119. The electronic storage 118 stores instructions, that when executed, cause a processor coupled to the source 105 to produce a beam 123, 125 directed at the region 107. Additionally, the electronic storage 118 may store predefined values that define parameters of the beam 123, 125 (e.g., energy, duration, and frequency) directed at the region 107.

The electronic storage 118 is one or more non-transitory electronic memory modules, and the electronic storage 118 may include non-volatile or persistent memory. The processor 117 may be a processor suitable for the execution of a computer program such as a general or special purpose microprocessor, and any one or more processors of any kind of digital computer. Generally, a processor receives instructions and data from a read-only memory or a random access memory or both. The processor 117 receives instruction and data from the components of the system 100, such as, for example, a location and/or other indication of the object 102. In some implementations, the system 100 includes more than one processor.

The input/output module 119 may be any device or module able to transmit data to, and receive data from, the system 100. For example, the input/output device 119 may be a mouse, a touch screen, a stylus, a keyboard, or any other device that enables a user to interact with the system 100. In some implementations, the input/output module 119 may be configured to receive an input from an automated process or a machine and/or configured to provide an output to an automated process or a machine.

In the example shown in FIG. 1, the object 102 moves through the region 107 in a direction 121. The object 102 may be mounted on a conveyor, movable platform, on wheels, or otherwise movable such that the object 102 passes through the region 107 in the direction 121. The conveyor may be multi-directional such that the conveyor may move the object 102 in a direction other than the direction 121. The conveyor may move the object 102 continuously, substantially continuously, or in a step-and-scan mode. The conveyor may rest in a particular place to allow a certain portion of the object 102 to be scanned ("spot scan"), or the conveyor may move such that the entire object 102, or the entire portion of the object 102 is scanned ("primary scan").

In some implementations, the source 105 and the detector 110 move together and relative to the object 102. In these implementations, the source 105 and/or the detector 110 may be mounted on a structure (not shown) such as a gantry or on tracks on the interior of a tunnel that receives luggage.

In the illustrated example, the source 105 is a single source that produces a beam having a neutron constituent 123 combined with a photon constituent 125. The neutron constituent 123 is a stream of neutron particles, and the photon constituent 125 is a stream of photon particles. In some examples, the photons are gamma-ray photons. However, it will be appreciated that X-ray photons can also be utilized in one or more embodiments. In some examples, the beam may be isolated, e.g., separated from other beams. The neutron and photon streams, which together form the beam, are generated simultaneously and fully integrated with one another so as to be collinear, traveling along a shared path. In this example, such neutron and photon streams are created by a single source that generates the beam. This configuration allows the streams of neutron and photon particles to be aimed at a common target area without accumulating path registration or time delay errors. A particular advantage may be that, because the neutron and photon streams are collinear and generated simultaneously, the resulting particle-enhanced images may be more accurate than a system that produces neutrons and photons from different sources from different locations and/or at different times. Other advantages may include lower cost, lower complexity, and easier control because dual source interference is not produced. In addition, such an arrangement may result in a source and a material discrimination system that is more compact and faster than a system that relies on multiple, discrete sources, each of which produces a particular type of particle (e.g., either neutrons or photons individually).

Figure 8A:
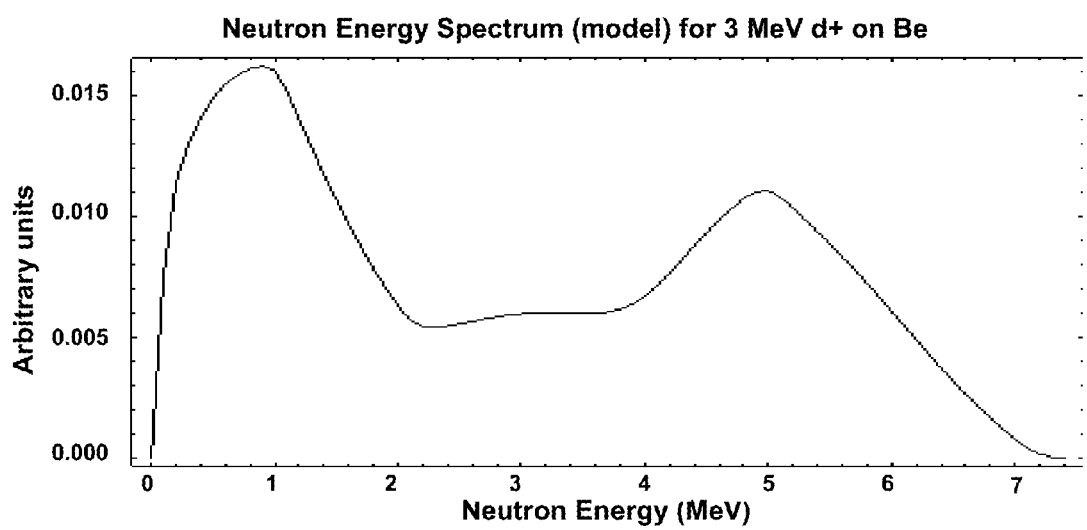
FIG. 8A is an example neutron energy spectra model.
Figure 8B:
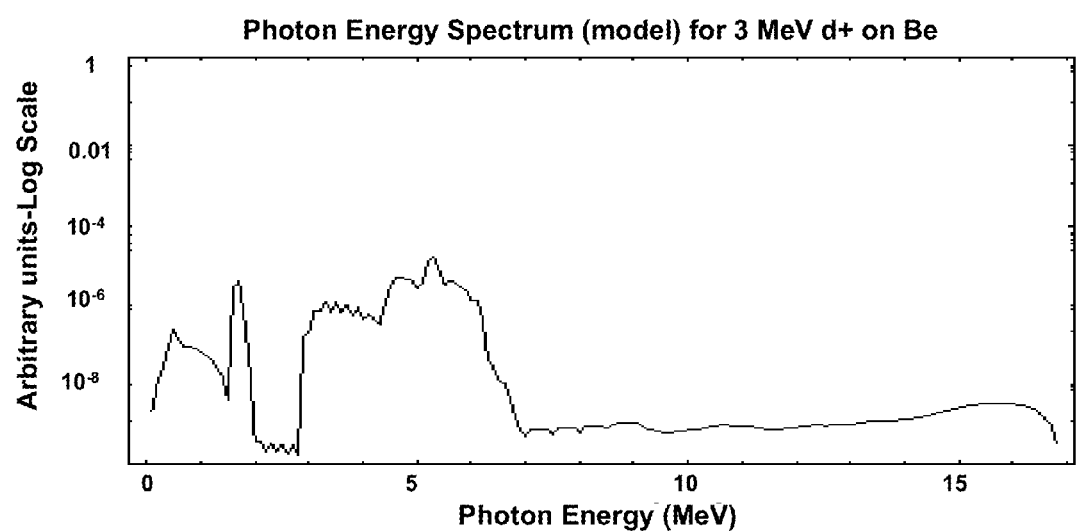
FIG. 8B is an example photon energy spectra model.

The neutron and photon constituents 123, 125 of the isolated beam can have a broad energy distribution or spectrum. For instance, in the case of a 3.0 MeV deuteron incident of beryllium (Be), the energy distribution of the neutron constituent 123 can range approximately between nearly 0 MeV and 7.3 MeV (see FIG. 8A). The energy distribution of the photon constituent 125 can range approximately between nearly 0 MeV and 16.9 MeV (see FIG. 8B).

The neutron constituent 123 of the isolated beam can provide a relatively high neutron flux, so that proper dosage levels for interrogation of the object 102 can be achieved without requiring an extended exposure time. In some examples, the neutron flux of the neutron constituent 123 can range approximately between $10^9$ neutrons/cm$^2$ sec and $10^{11}$ neutrons/cm$^2$ sec. For similar reasons, the photon constituent 125 of the isolated beam can provide a relatively high photon flux. In some examples, the photon flux of the photon constituent 125 can range approximately between $10^5$ photons/cm$^2$ sec and $10^8$ photons/cm$^2$ sec.

The single source 105 may include a particle accelerator 130 and a target 132 designed to create a predefined type of nuclear reaction that produces a beam that includes both neutrons and photons. In particular, the accelerator 130 is designed to bombard the target 132 with energized particles to induce nuclear reactions that yield the neutrons and photons. The type of nuclear reactions generated by the source 105 is directly related to the materials used (e.g., the type of particles energized by the accelerator and/or the type of target material provided).

In one example, the target 132 is a solid, non-radioactive Be target that produces photons and neutrons in response to a bombardment of deuterons from the accelerator. Various other types of accelerators (e.g., proton accelerators) and targets (e.g., boron targets, lithium targets, gaseous targets, etc.) can be used to generate nuclear reactions that produce both photons and neutrons. For example, a deuterium or tritium target with a modified window 134 can be used. The modified window 134 may be composed of, for example, carbon-12 that produces photons when impinged by deuterons. The output energy of the accelerator can also affect the yields of nuclear reactions that are induced, and thus the characteristics of neutron-photon yield. For example, a target bombarded with relatively high energy particles would produce different neutron-photon beam than if an accelerator providing relatively low energy particles were used. In one example, a 3 MeV accelerator could be used to energize deuteron particles.

Various process parameters (including those described above) can be tuned to achieve desired types of nuclear reactions that yield an isolated, mixed neutron-photon beam with specific characteristics, such as those discussed above. In one particular example a 3.0 MeV deuteron may be used with a Be target. The accelerator could be a fixed energy, fixed particle type RFQ accelerator. An RFQ accelerator is not required but may be useful and practical to generate optimal neutron and photon energy spectra. The resulting neutron flux typically depends on the accelerator average beam current and particle energy, but could be as high as 10^11 n/sec. In particular, the accelerator beam energy has a strong influence on the emitted neutron and photon energies.

In some implementations, the single source 105 may produce, alternatively or in addition to the neutrons and the photons, a second combined neutron-photon beam, where the second beam is substantially different from the first by using a second production target. The source 105 may produce more than two neutron beams, each having a different mean energy or energy distribution. Thus, the source 105 may be a multi-energy neutron beam source that produces dual-energy, or broad spectrum energy, neutron beams from a single energy deuteron accelerator. In these implementations, the source 105 may include two or more neutron production targets (not shown). The source 105 may be switchable between a state that produces two distinct combined photons and neutron beams.

The neutron constituent 123 and the photon constituent 125 are directed towards the region 107 and penetrate through a first side 128 the object 102, which attenuates the photons and the neutrons, resulting in an attenuated neutron constituent 123' and an attenuated photon constituent 125' that emerge from a second side 129 of the object 102.

The detector 110 is a detector or a type of imaging array that detects both the attenuated neutrons and the attenuated photons. The detector 110 is a detector that is made from a material that interacts with incoming neutrons and photons to produce a signal (such as an electrical signal or light), and the material interacts differently with photons than with neutrons. For example, the detector 110 may include a plastic scintillator in which both neutrons and photons interact. The signal from the detector 110 is provided to the imaging module 115 for analysis and processing, and the electronic processor 118 of the imaging module 115 may assign a value to the signal based on, for example, the magnitude or the shape of the signal or another property that is related to the type of detected particle that caused the signal to be generated.

Because the property of the signal is indicative of the type of particle detected, a windowed discriminator may be used to distinguish signals arising from photons from those arising from neutrons. The windowed discriminator may include at least two thresholds of different values, with each threshold being associated with a value. For example, the windowed discriminator may include a first threshold having a first value, and a second threshold having a second value that is greater than the first value. In some implementations, the first value may be about 10 mV, and the second value may be about 150 mV. The windowed discriminator may accept signals that are above the first threshold and below the second threshold. In some implementations, the windowed discriminator only accepts signals that have a peak value greater than or equal to the first threshold and equal to or lower than the second threshold. The values of the two thresholds of the windowed discriminator and the detector voltage (the voltage of the imaging array or detector 110) may be adjusted.

In some examples, the windowed discriminator includes more than two threshold values. For example, the windowed discriminator can include multiple low and high threshold values, a first set of values (i.e., one low threshold value and one high threshold value) relating to photon energies and a second set of values relating to neutron energies. In this case, two separate "windows" of detection are provided, each of the windows being specifically tuned for detecting attenuated photons or neutrons.

Signals that are above the first threshold but below the second threshold may be deemed to be signals that result from neutrons or photons. At a typical detector voltage, neutron signals tend to be smaller than photon signals. In these instances, the neutron signals may be greater than or equal to the first threshold value and less than or equal to the second threshold value such that the neutron signals are accepted by the windowed discriminator and detected as a neutron signal. Lowering the detector voltage may allow detection of photon signals without changing the first and second threshold values. Alternatively, increasing the first and second threshold values, without necessarily lowering the detector voltage, may allow detection of the relatively larger photon signals. Thus, photon and neutron signals from the single imaging array 110 may be discriminated from each other. The imaging module 115 produces a photon image based on the signals deemed to result from the detection of photons, and a neutron image based on the signals deemed to result from the detection of neutrons.

The photon and neutron images may be obtained through various techniques. The gain and threshold of the single detector 110 may be optimized for neutron detection or for photon detection, by for example, changing the detector gain. In some implementations, to generate the neutron image and the photon image, the object 102 may be scanned twice, once with the detector 110 optimized for neutron detection and once with the detector 110 optimized for photon detection. In some implementations, the settings of the detector 110 may be toggled to detect for a fixed percentage of time (such as, for example, 50%) with the settings optimized for detecting neutrons and the remaining amount of time with the settings optimized for detecting photons. In this implementation, the detections of neutrons and photons may be separated with post-processing, such as the windowed discriminator discussed above. In some implementations, the single imaging array or single detector 110 may include two portions displaced laterally along the direction 121, with one portion optimized for detecting neutrons and the other portion optimized for detecting photons.

Figure 2A:
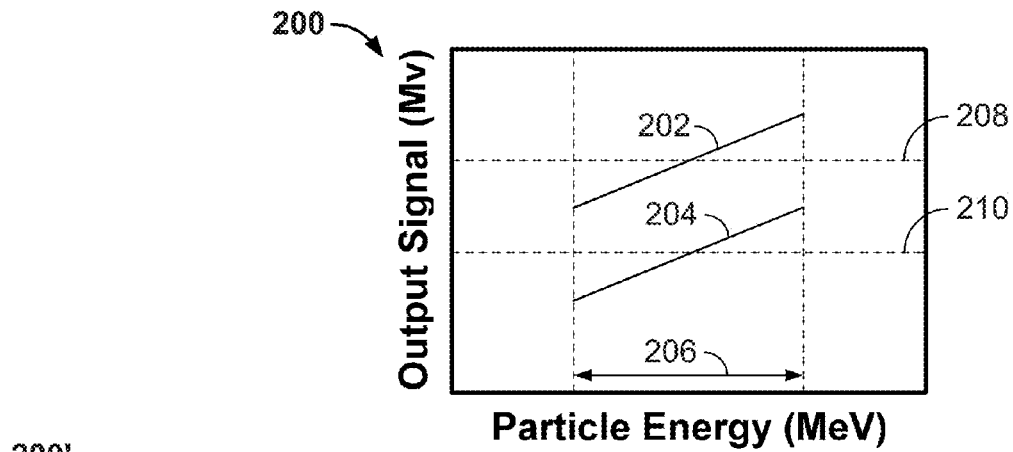
FIGS. 2A-2C are hypothetical graphs relating detector output signal to particle energy, such as may be ascertained using the detector included in the material discrimination system of FIG. 1.
Figure 2B:
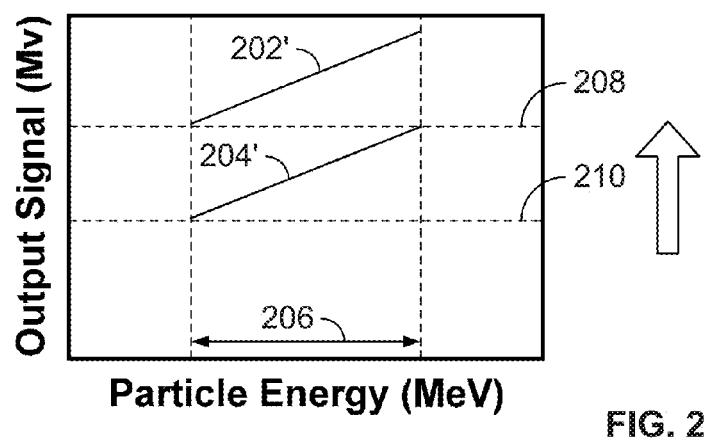
Figure 2C:
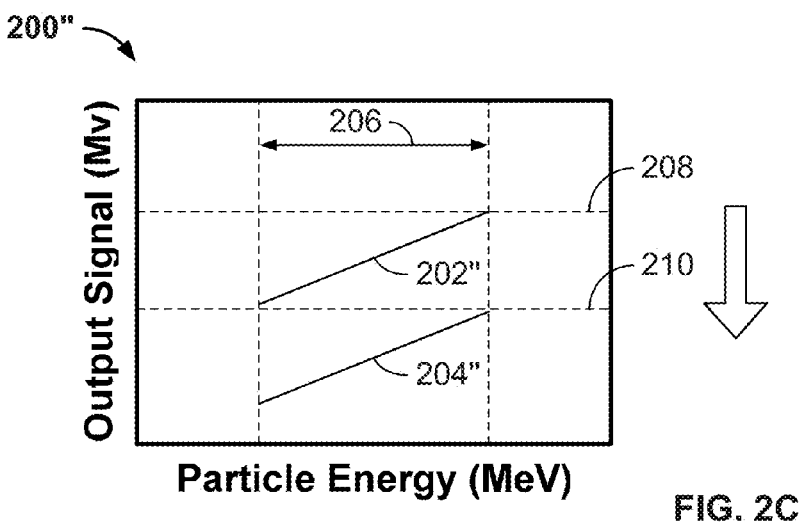

Together, FIGS. 2A-2C illustrate an example technique for distinguishing signals arising from neutrons and photons respectively. FIG. 2A shows a first hypothetical graph 200 relating particle energy to detector output signal, which corresponds to the configuration of FIG. 1, where the detector 110 receives neutrons and photons generated by the single source 105 and attenuated by the object 102. Note that the hypothetical graph 200 is not necessarily indicative of empirical or theoretical data, but is used solely for illustrating one or more embodiments of the present disclosure. The graph 200 includes a photon curve 202 and a neutron curve 204 representing the signal response for photons and neutrons, respectively, within an energy spectrum 206. In this case, with the output signal being unadjusted, the photon curve 202 traverses the upper threshold value 208, and the neutron curve traverses the lower threshold value 210. As such, it may be difficult to distinguish between the attenuated neutrons and photons interacting with the detector.

FIG. 2B shows a second hypothetical graph 200' where the output signal is altered by a positive gain (i.e., a gain greater than one), while the threshold values 208 and 210 remain constant. In this case, the photon curve 202' is boosted above the upper threshold value 208, and the neutron curve 204' is situated between the upper threshold value and the lower threshold value 210. In this example, the detector 110 is optimized for neutron detection. In this example, the detector 110 is optimized for neutron detection, such that an adjusted value of the output signal can be compared to the upper and lower threshold values 208 and 210 to determine whether the signal represents detection of a neutron. That is, if adjusted output signal is between the upper and lower threshold values 208 and 210, the detector can determine that the signal represents detection of a neutron.

FIG. 2C shows a third hypothetical graph 200" where the output signal is altered by a negative gain (i.e., a gain less than 1). Again, the threshold values 208 and 210 remain constant. In this case, the neutron curve 204" is diminished below the lower threshold value 210, while the photon curve 202" is situated between the lower threshold value and the upper threshold value 208. In this example, the detector 110 is optimized for photon detection, such that an adjusted value of the output signal can be compared to the upper and lower threshold values 208 and 210 to determine whether the signal represents detection of a photon. That is, if adjusted output signal is between the upper and lower threshold values 208 and 210, the detector can determine that the signal represents detection of a photon.

In the above described example, the output signals of the detector 110 were altered to appropriately optimize the detector. However, various other techniques can also be used. For example, either or both of the threshold values can be altered to optimize the detector for neutron or photon detection. In some examples, the threshold values and the output signals can be altered for this purpose.

Figure 3:
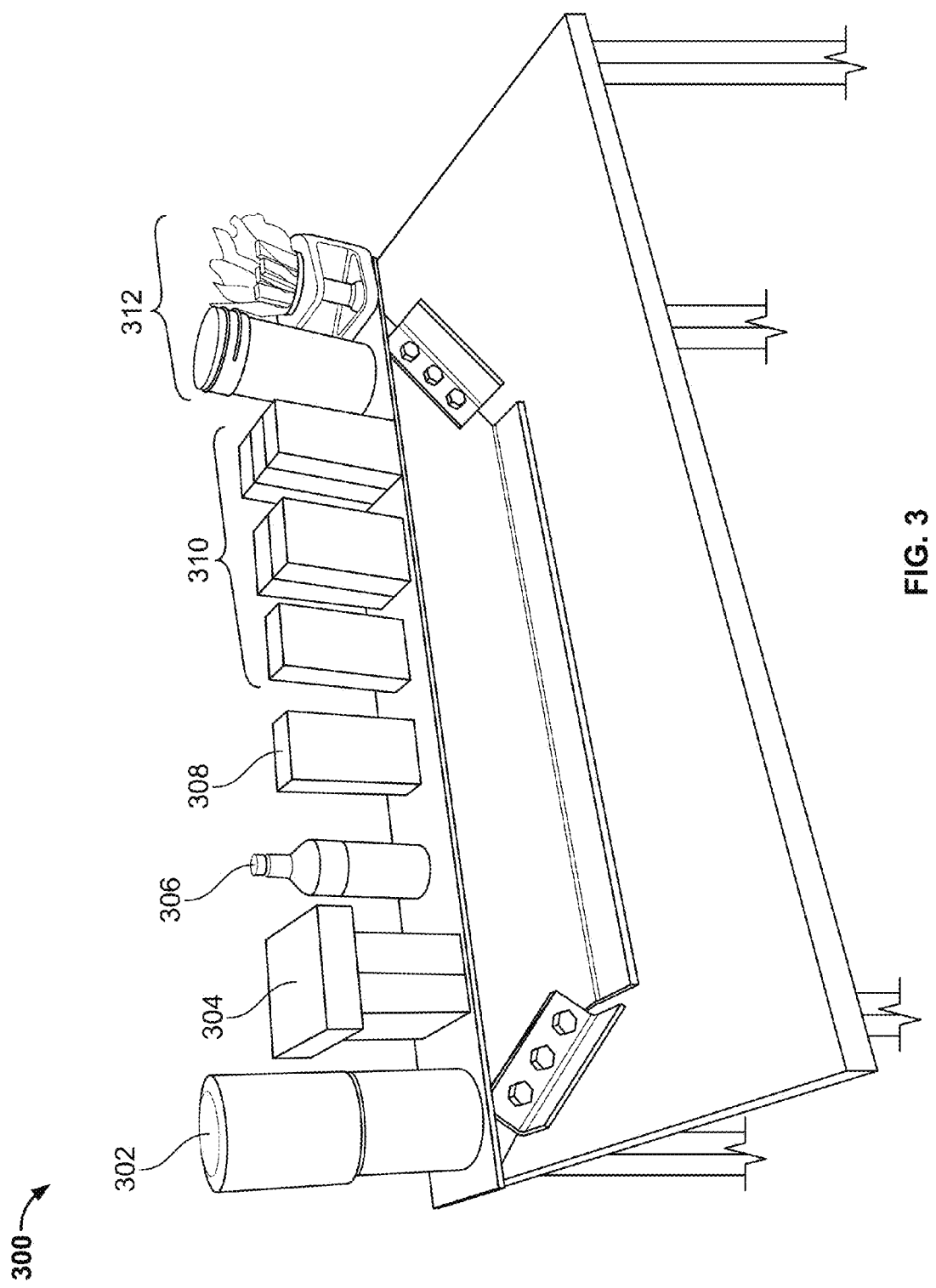
FIG. 3 is a first example arrangement of objects to be scanned by a material discrimination system.
Figure 4A:
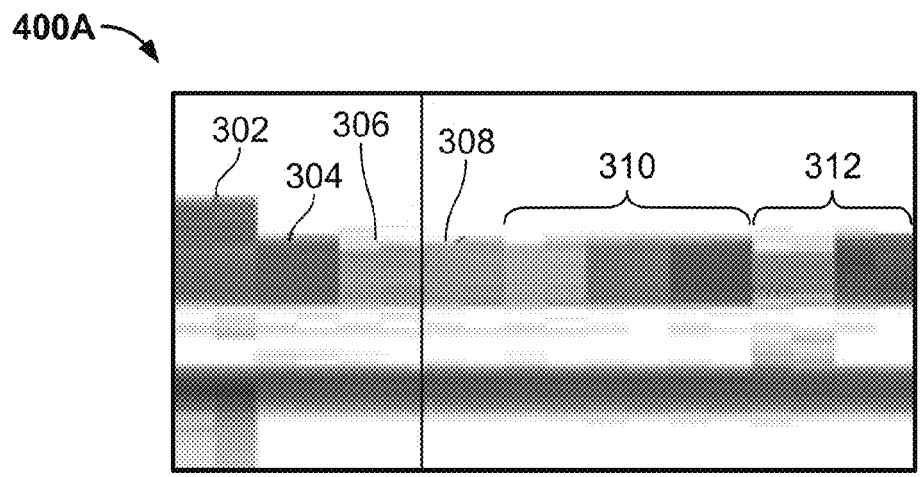
FIG. 4A is a neutron-enhanced image of the objects of FIG. 3.
Figure 4B:
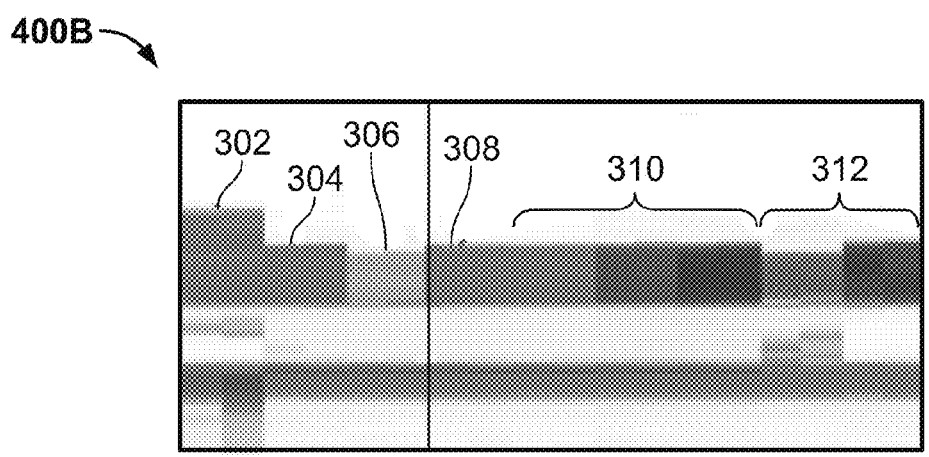
FIG. 4B is a photon-enhanced image of the objects of FIG. 3.
Figure 4C:
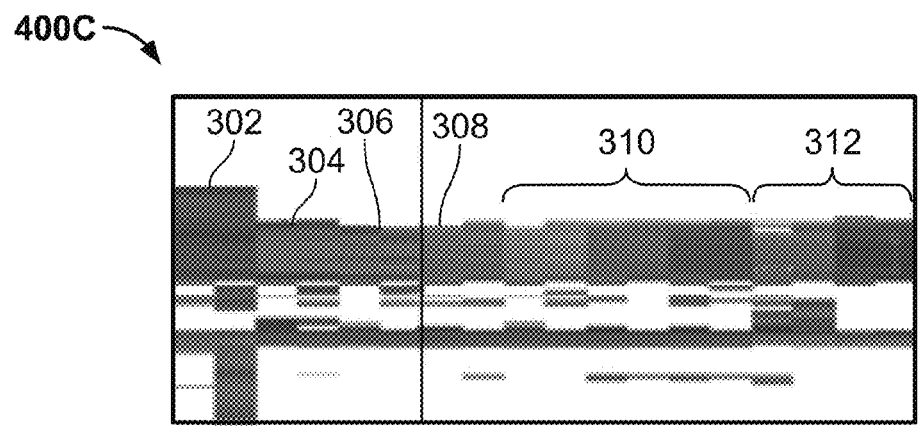
FIG. 4C is a comparative image based on a ratio of the neutron-enhanced image of FIG. 4A and the photon-enhanced image of FIG. 4B.

FIG. 3 shows a first example arrangement 300 of sample objects 302-312 that can be scanned and discriminated by the system 100. In particular, the object 302 is Aluminum; the object 304 is Teflon; the object 306 is water; the object 308 is steel; the object 310 is lead; and the object 312 is uranium. FIG. 4A shows an example of a neutron image 400A, FIG. 4B shows an example of a photon image 400B, and FIG. 4C shows an example of a ratio between the neutron image 400A and the photon image of 400B. The images 400A and 400B are images of the sample objects 302-312, such as can be generated by the system 100 to facilitate determination of whether the objects include materials that are low-Z, high Z, or both.

As noted above, low-Z materials (such as organic material) attenuate neutrons more strongly than photons. Thus, any of the objects 302-312 that hold low-Z materials are darker in the neutron image 400A than the same objects in the photon image 400B. The reverse is true for high-Z materials (such as steel and uranium) because high-Z materials attenuate photons more strongly than neutrons. The ratio of the images 400A and 400B produces an image 400C (FIG. 4C) that shows the relative Z of the objects 302-312. In this case, the left portion of the image 400C corresponds to objects 302-306, which hold organic and inorganic materials that have a relatively low-Z. The right portion of the image 400C corresponds to objects 308-312, which hold metallic, high-Z materials.

The image 400C may be color-coded to assist the operator of the system 100 (or an automated process that monitors data from the system 100) in identifying high-Z and low-Z regions in the image 400C (and hence in the set of objects 302-312). For example, low-Z materials may be color coded with a gold or brown color, and high-Z materials may be color coded with a blue color. The color coded image may be shaded to show variations of Z within high-Z and low-Z regions.

All or some of the images 400A, 400B, and 400C may be displayed to an operator of the system 100 on the display 119. The images 400A, 400B, 400C may be presented with other techniques. For example, the images may be printed, uploaded to a remote site, or emailed from the system 100.

Figure 6A:
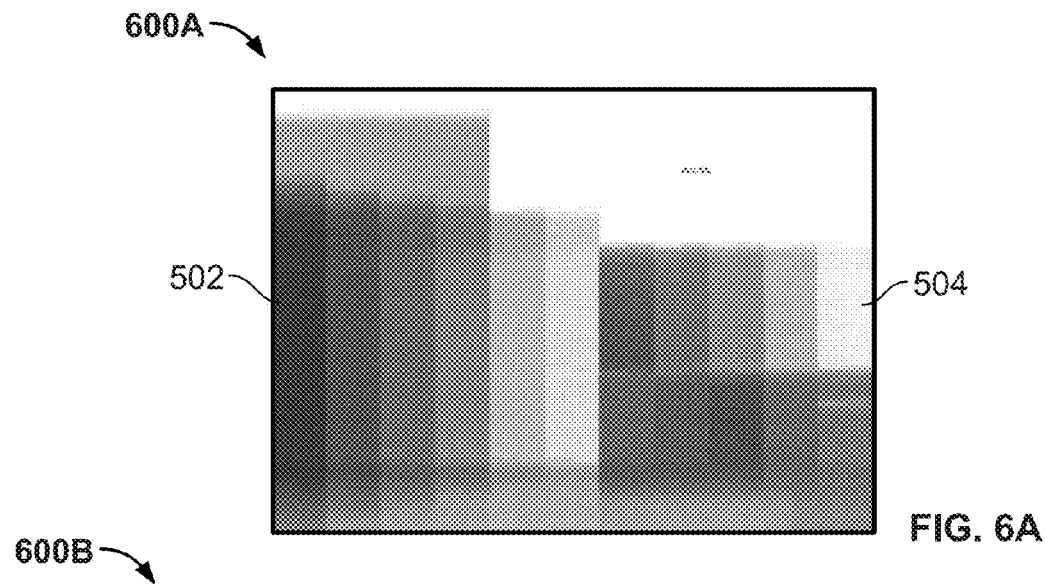
FIG. 6A is a neutron-enhanced image of the objects of FIG. 5.
Figure 6B:
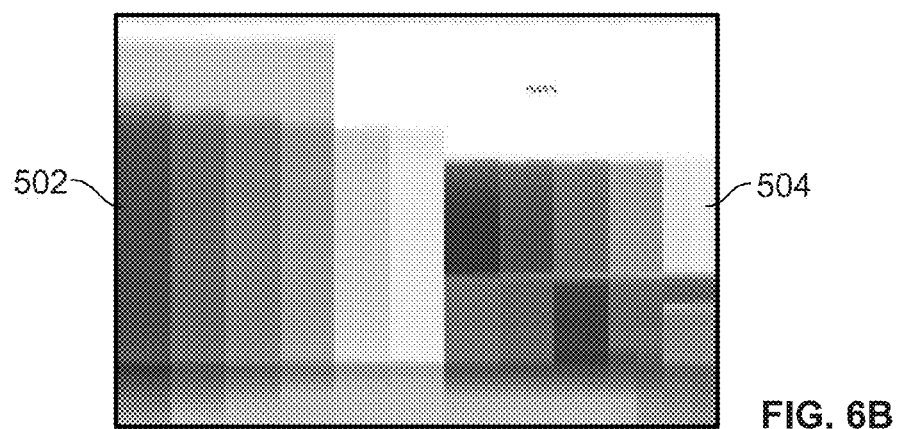
FIG. 6B is a photon-enhanced image of the objects of FIG. 5.
Figure 6C:
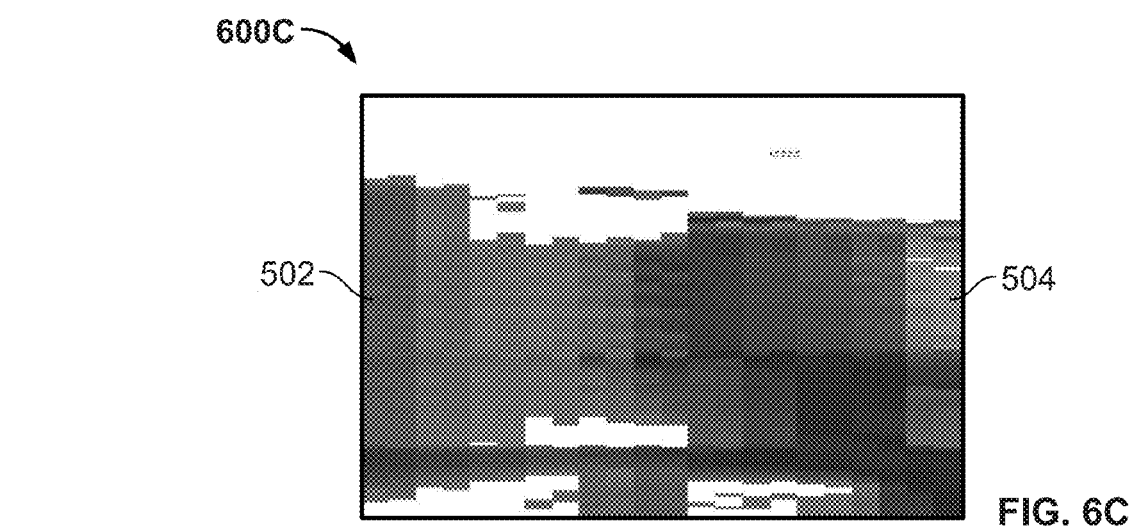
FIG. 6C is a comparative image based on a ratio of the neutron-enhanced image of FIG. 6A and the photon-enhanced image of FIG. 6B.

FIG. 5 shows a second example arrangement 500 of sample 502 and 504 that can be scanned and discriminated by the system 100. In this case, the object 502 is polyethylene and the object 504 is steel. FIGS. 6A, 6B, and 6C show examples of images that may be produced from data collected by the system 100. In the examples of FIGS. 6A-6C, the system 100 produces photons in the form of gamma rays. FIG. 6A shows a neutron image 600A, FIG. 6B shows a gamma image 600B, and FIG. 6C shows a ratio of the neutron image 600A and the gamma image 600B. A comparison of FIGS. 6A and 6B shows the differences in polyethylene's absorption of neutrons and gamma rays, with neutrons being more strongly absorbed (or attenuated) because polyethylene is a relatively low-Z material. In contrast, steel attenuates gamma rays more than neutrons. Thus, the steel object 504 appears lighter in the neutron image 600A than in the gamma image 600B. The image 600C is the ratio of the neutron image 600A and the gamma image 600B. The shading of the image 600C near the top is representative of low-Z material and the shading near the bottom of the image 600C is representative of high-Z material. In the examples shown in FIGS. 6A-6C, the images are the log-normalized attenuation of a particle (neutron or gamma ray) attenuated by the objects 502 and 504. The ratio image 600C may be color-coded as discussed above with respect to FIG. 4C. The images are step wedges and show that the material discrimination works independent of the material thickness.

In some implementations, dosage rates around the system 100 may be monitored with scattered radiation monitors (not shown) to ensure that the dosage rate around the system 100 is within an acceptable limit.

Figure 7:
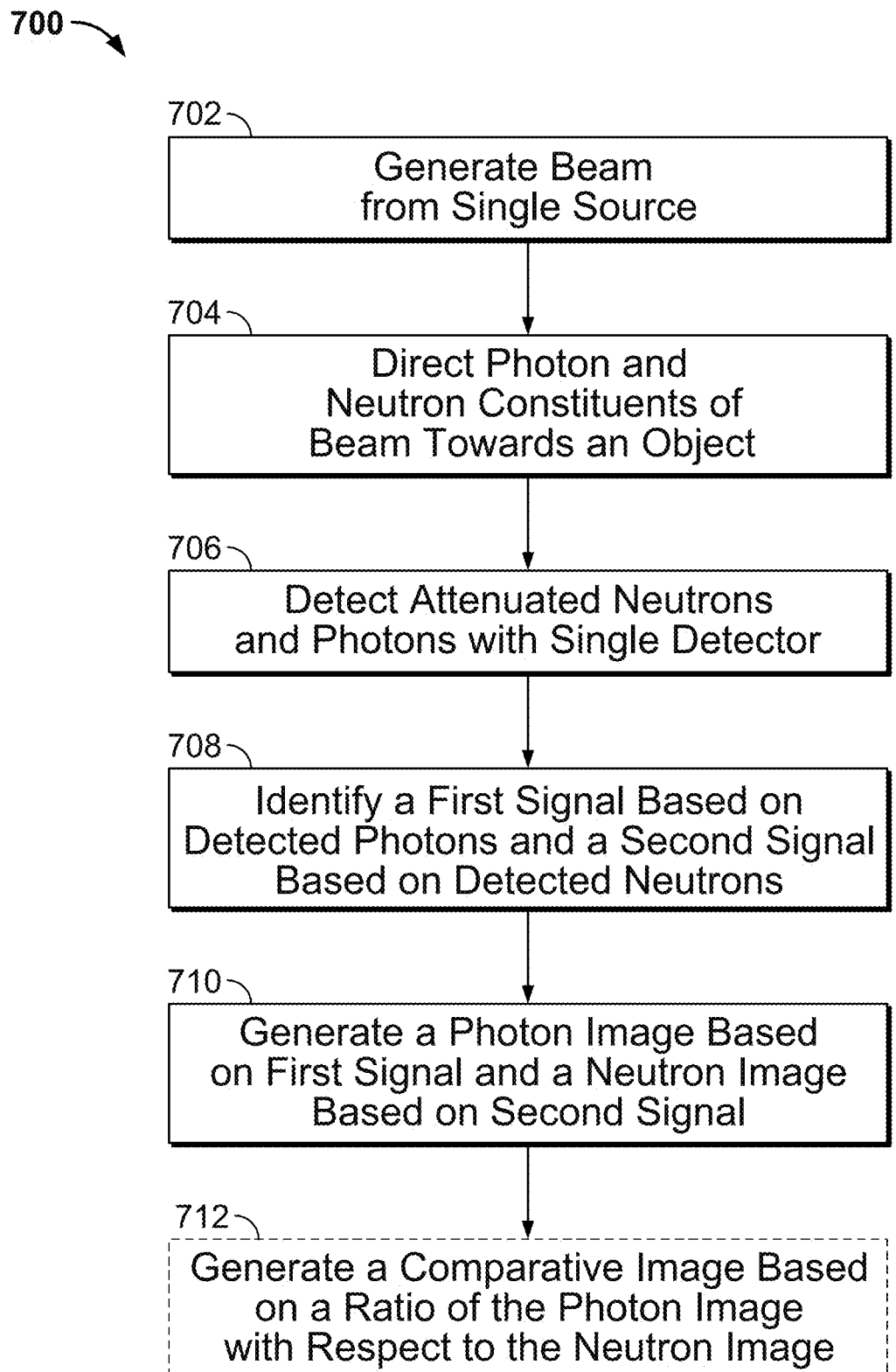
FIG. 7 is a flow chart illustrating an example process for facilitating material discrimination.

FIG. 7 illustrates an example process 700 for material discrimination. The process 700 can be implemented, for example, using the system 100 described above. As shown, process 700 begins at step 702, when a beam is generated from a single source. The beam can include a photon constituent stream of particles and a collinear neutron constituent stream of particles. At step 704, the neutron and photon constituents of the beam are directed towards an object of interest. At step 706, attenuated neutrons and photons that pass through the object are detected with a single detector. The single detector can include a single imaging array responsive to both neutrons and photons. At step 708 a first signal primarily based on detected photons is identified, and a second signal primarily based on detected neutrons is identified. It should be noted that the signals substantially represent the corresponding particle type (e.g., photon or neutron) but may contain some contamination from other particle types. Thus, the signals are based primarily on detected particles of the identified type, but there may be a percentage of particles of other types (e.g., up to about 40%). It should be appreciated that the lower the fraction of contaminating particles, the better the material discrimination performance of the system. In some examples, a windowed discriminator can be used to distinguish between a signal associated with the detection of photons and a signal associated with detection of neutrons. At step 710, a photon-enhanced image is generated based on the first signal, and a neutron-enhanced image is generated based on the second signal. Finally, at optional step 712, a comparative image is generated based on a ratio between the photon-enhanced image and the neutron-enhanced image.

A number of implementations have been described in the context of various examples. Nevertheless, it will be understood that various modifications may be made without departing from the scope of the disclosure. It will be further understood that the present disclosure is not limited by the context of the examples described herein. For instance, although various examples are described with reference to large maritime cargo containers, one or more implementations of the present disclosure can be used in smaller application (e.g., luggage checkpoints at an airport, rail care and passenger car traffic at border entries, and the like).

The techniques discussed above may be implemented as a system, a method, a process, a device, or as software on a non-transitory computer-readable medium.

What is claimed is:

1. A materials discrimination system comprising:
   a single source that includes a single target, the single target configured to produce a beam comprising a neutron constituent and a photon constituent when struck by a deuteron, wherein the neutron constituent and the photon constituent are collinear;
   a single detector aligned with the single source along a path of the beam, the single detector configured to detect neutrons and photons present in the beam, and to produce a signal based on a detection of neutrons or photons, the signal being associated with a value; and
   a processor configured to:
   receive signals produced by the single detector;
   distinguish between signals that represent detection of a neutron and signals that represent detection of a photon;
   generate a first image of a region primarily based on detection of neutrons;
   generate a second image of the region primarily based on detection of photons;
   determine different effective atomic numbers for different portions of the region based on the ratio between (i) the first image of the region primarily based on detection of neutrons and (ii) the second image of the region primarily based on detection of photons;

generate the comparative image based on the determined different effective atomic numbers for the different portions of the region; and provide the comparative image for display to an operator.

2. The system of claim 1, wherein the processor is configured to distinguish between signals that represent detection of a neutron and signals that represent detection of a photon based on comparing the value associated with a signal to a first threshold value and a second threshold value, the second threshold value being greater than the first threshold value.

3. The system of claim 2, wherein the processor is configured to distinguish between signals that represent detection of a neutron and signals that represent detection of a photon based on a window defined by low and high thresholds for photons and a different, separate window defined by different, low and high thresholds for neutrons.

4. The system of claim 1, wherein the single target comprises a beryllium target that produces the neutron constituent and the photon constituent when struck by the deuteron.

5. The system of claim 4, wherein the single source is further configured to produce multi-energy neutrons, and the single source further comprises a second target.

6. The system of claim 1, wherein the photons comprise gamma-ray photons.

7. The system of claim 1, wherein the photons comprise x-ray photons.

8. The system of claim 1, wherein the single source and the single detector are mounted on a structure comprising an opening configured to receive a cargo.

9. The system of claim 8, further comprising a conveyor configured to move the cargo through the structure and relative to the single source and the single detector.

10. The system of claim 1, wherein the system is re-locatable.

11. The system of claim 1, wherein the neutron constituent and the photon constituent comprise a broad energy distribution.

12. The system of claim 1, wherein the neutron constituent comprises a flux ranging between approximately $10^9$ neutrons/$cm^2$ sec and $10^{11}$ neutrons/$cm^2$ sec.

13. The system of claim 1, wherein the photon constituent comprises a flux ranging between approximately between $10^5$ photons/$cm^2$ sec and $10^8$ photons/$cm^2$ sec.

14. The system of claim 1, wherein the processor is configured to:

color code the different portions of the comparative image based on the determined different effective atomic numbers for different portions of the region.

15. A system for material discrimination comprising:

a single source that includes a single target, the single target configured to produce a beam comprising a neutron constituent and a photon constituent when struck by a deuteron, wherein the neutron constituent and the photon constituent are collinear;

a single imaging array aligned with the single source along a path of the beam, the single imaging array configured to detect neutrons and the photons produced by the single source, and to produce a signal based on a detection of neutrons or photons, the signal being associated with a value; and a processor configured to:

receive signals produced by the single imaging array, distinguish between signals that represent detection of a neutron and signals that represent detection of a photon;

generate a first image of a region primarily based on detection of neutrons, generate a second image of the region primarily based on detection of photons, determine different effective atomic numbers for different portions of the region based on the ratio between (i) the first image of the region primarily based on detection of neutrons and (ii) the second image of the region primarily based on detection of photons;

generate the comparative image based on the determined different effective atomic numbers for the different portions of the region; and provide the comparative image for display to an operator.

16. The system of claim 15, further comprising a display configured to present one or more of the first image or the second image.

17. A method of material discrimination comprising:

generating, from a single target of a single source, a beam comprising a neutron constituent and a photon constituent when the single target is struck by a deuteron, wherein the neutron constituent and the photon constituent are collinear;

directing the beam towards a first side of an object to be imaged;

detecting, at a single imaging array on a second side of the object, photons and neutrons;

generating a first image of a region primarily based on detection of neutrons;

generating a second image of the region primarily based on detection of photons;

determining different effective atomic numbers for different portions of the region based on the ratio between (i) the first image of the region primarily based on detection of neutrons and (ii) the second image of the region primarily based on detection of photons;

generating the comparative image based on the determined different effective atomic numbers for the different portions of the region; and providing the comparative image for display to an operator.

18. The method of claim 17, further comprising:

outputting a graphical representation of one or more of the first image or the second image.

19. The method of claim 17, wherein the first side of the object and the second side of the object are opposite sides of the object.

* * * * *